(12) United States Patent
Chang et al.

(10) Patent No.: US 9,018,203 B2
(45) Date of Patent: Apr. 28, 2015

(54) PHARMACEUTICAL COMPOSITION OF SALICYLANILIDE-DERIVED SMALL MOLECULES AND PREPARATION AND APPLICATION THEREOF

(75) Inventors: Deh-Ming Chang, Taipei (TW);
Hsu-Shan Huang, Taipei (TW);
Chun-Liang Chen, Taipei (TW);
Chia-Chung Lee, Taipei (TW)

(73) Assignee: National Defense Medical Center, Taipei (TW)

( * ) Notice: Subject to any disclaimer, the term of this patent is extended or adjusted under 35 U.S.C. 154(b) by 164 days.

(21) Appl. No.: 13/610,489

(22) Filed: Sep. 11, 2012

(65) Prior Publication Data
US 2013/0281412 A1    Oct. 24, 2013

(30) Foreign Application Priority Data
Apr. 18, 2012   (TW) .............................. 101113754 A (51) Int. Cl.
*C07D 265/26* (2006.01)
*A61K 31/609* (2006.01)
*A61K 31/536* (2006.01)
*C07C 235/64* (2006.01)

(52) U.S. Cl.
CPC ............. *A61K 31/536* (2013.01); *A61K 31/609* (2013.01); *C07C 235/64* (2013.01); *C07D 265/26* (2013.01)

(58) Field of Classification Search
USPC ......................................... 544/94; 514/230.5
See application file for complete search history.

(56) References Cited

PUBLICATIONS

Stenseth et al. Journal of Medicinal Chemistry (1963), 6, 212-213.*

\* cited by examiner

*Primary Examiner* — Kahsay Habte
(74) *Attorney, Agent, or Firm* — Muncy, Geissler, Olds & Lowe, P.C.

(57) ABSTRACT

The present invention provides a pharmaceutical composition of salicylanilide-derived small molecules include:
(a) a compound which structure is selected from formula I or formula II:

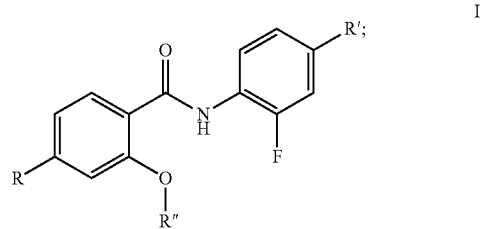

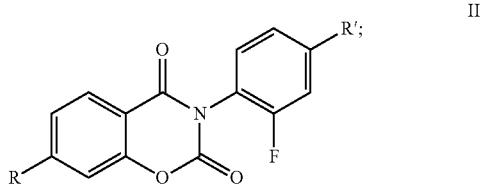

(b) a pharmaceutically acceptable salt and excipient. The present invention also provides the synthesis method of the pharmaceutical composition and the application thereof.

7 Claims, 2 Drawing Sheets

PHARMACEUTICAL COMPOSITION OF SALICYLANILIDE-DERIVED SMALL MOLECULES AND PREPARATION AND APPLICATION THEREOF

CROSS-REFERENCE TO RELATED APPLICATIONS

This Non-provisional application claims priority under 35 U.S.C. §119(a) on Patent Application No(s). [101113754] filed in Taiwan, Republic of China [Apr. 18, 2012], the entire contents of which are hereby incorporated by reference.

FIELD OF THE INVENTION

The present invention is related to a pharmaceutical composition of salicylanilide-derived small molecule, the synthesis method and the application thereof, especially related to the application of treating osteoporosis, osteoarthritis and inflammatory reaction.

BACKGROUND OF THE INVENTION

The recent studies showed that many small molecules have the inhibitory activity of NF-κ B, such as salicylanilide and aspirin. The mechanism would strongly affect the inhibition of osteoclastogenesis. In other natural compounds, such as Paeonol from *Paeonia lactiflora Pallas*, Ikarisoside A from *Epimedium koreanum*, Bavachalcone from *Psoralea corylifolia*, etc., could inhibit osteoclastogenesis. Besides, Indeno[1,2-c]quinoline derivatives, Benzopyranyl Tetracycles derivatives and 3-Amino-2-hydroxypropoxyisoflavone derivatives are also found have the inhibition ability. However, the mechanism and effect is still unclear. Therefore, synthesizing more compounds, which can be applied to inhibit osteoclastogenesis, could have a potent to inhibit the development of anti-osteoporosis drugs.

In the bone regeneration process, once the balance of the bone remodeling is broken, the bone resorption of the osteoclasts is dominated over bone formation of the osteoblasts, the bone remodeling would be imbalanced. As a result, osteocytes, osteopenia and bone mineral density are decreased, and then induce lots of bone diseases, such as osteoporosis, periodontitis or osteoarthritis.

The osteoclasts are developed from hematopoietic precursor cells. Further, the Macrophage-Colony Stimulating Factor (M-CSF) and Receptor Activator of Nuclear factor Kappa B Ligand (RANKL) are secreted by osteoblast. They can combine with the c-Fms and RANK on the cell membrane of the osteoclast precursor cells, and then induce the secretion of tartrate-resistant acid phosphatase (TRAP), integrin β3 expression, and actin ring formation, etc. These proteins enhance the osteoclasts motility and adhere on the bone surface. In addition, the expression of cathepsin K matrix metalloproteinase-9 (MMP-9), dendritic cell-specific transmembrane protein (DC-STAMP), ATPase, $H^+$ transporting lysosomal V0 subunit D2 (ATP6V0D2) also induce the osteoclast precursor cells into the matured (diameter is 20-100 mm) multinucleated cells (MNCs) (containing 4-20 nucleus), which have the bone resorption function. Besides, osteoblasts not only secret M-CSF and RANKL, which induce the osteocytes growth and differentiation, but also secret the osteoprotegerin (OPG). OPG is associated with RANKL to prevent the association of RANKL and RANK. Hence, it prevents and inhibits the formation of osteoclasts, decreases the bone resorption.

SUMMARY OF THE INVENTION

For the purpose, the present invention provides a series of pharmaceutical compositions of salicylanilide-derived small molecule, wherein the pharmaceutical compositions can be used for treating inflammatory reaction, and preventing osteoporosis and osteoarthritis effectively.

The present invention provides a salicylanilide-derived small molecule, which structure is selected from formula I or formula II:

The present invention provides a pharmaceutical composition of salicylanilide-derived small molecule, which comprises:

(a) a compound, which structure is selected from formula I or formula II:

(b) a pharmaceutical acceptable salt and carrier of the compounds.

Preferably, the R of the formula I or formula II is selected from the group of H and OCxHy, wherein the x and y of the OCxHy is any positive integer; the R' of the formula I or formula II is selected from the group consisting of Halogen, wherein the Halogen is F, Cl, Br, I or At; the R" of the formula I is selected from the group consisting of H, OCxHy and 2,4-difluorobenzyl, wherein the x and y of the OCxHy is any positive integer.

Preferably, the pharmaceutical acceptable carrier is excipient, diluents, thickeners, filler, binder, disintegrants, lubri- cant, oil or non-oil base, surfactant, suspending agent, gelling agent, adjuvant, anti-corrosive agent, anti-oxidant, stabilizer, coloring agent or flavor.

Preferably, the salt can be physiological acceptable salt of inorganic acid, inorganic base, organic acid or organic base.

Preferably, the composition can be powder, granule, liquid, gel or cream.

Preferably, the composition is administrated through oral, transdermal, injection, or inhalational manner.

The present invention provides a synthesis method of pharmaceutical composition of salicylanilide-derived small molecule, wherein a compound of formula I is synthesized by a compound of formula III:

Preferably, the R of the formula I or formula III is selected from the group consisting of H and OCxHy, wherein the x and y of the OCxHy is any positive integer; the R' of the formula I is selected from the group consisting of Halogen, wherein the Halogen is F, Cl, Br, I or At; and the R" of the formula I is selected from the group consisting of H, OCxHy and 2,4-difluorobenzyl, wherein the x and y of the OCxHy is any positive integer.

The present invention also provides a synthesis method of pharmaceutical composition of salicylanilide-derived small molecule, wherein a compound of formula II is synthesized by a compound of formula I:

Preferably, the R of the formula I or formula II is selected from the group consisting of H and OCxHy, wherein the x and y of the OCxHy is any positive integer; R' is selected from the group of Halogen, wherein the Halogen is F, Cl, Br, I or At; and the R" of the formula I is H.

Preferably, the compound of formula III is salicylic acid, and the compound of formula III, tetrahydrofuran and thionyl chloride can synthesize an intermediate, the intermediate, amine and tetrahydrofuran can synthesize the compound of formula I.

Preferably, the said amine is 4-chloro-2-fluorobenzenamine or 2,4-difluoroaniline.

Preferably, the compound of formula II is synthesized by the compound of formula I, anhydrous pyridine and methyl chloroformate.

Preferably, the pharmaceutical composition can be used as an osteoporosis therapeutic agent, an osteoarthritis therapeutics agent or an anti-inflammatory agent.

BRIEF DESCRIPTION OF THE DRAWINGS

FIG. 1A shows the normal RAW 264.7 cells without treated with RANKL.

FIG. 1B shows the RAW 264.7 cells treated with RANKL.

FIG. 1 C, D, E is the schematic showing of the osteoclasts generation amount of RAW264.7 cells with different compounds (10 μM).

FIG. 2A shows the erosion of bone slices in RAW 264.7 cells without the presence of RANKL.

FIG. 2B shows the erosion of bone slices in RAW 264.7 cells in the presence of RANKL.

FIGS. 2C and D show the erosion of bone slices in RAW 264.7 cells in the presence of different compounds (10 μM).

DETAILED DESCRIPTION OF THE INVENTION

The present invention provides a series of pharmaceutical compositions of salicylanilide-derived small molecule, which can be used to inhibit the formation of osteoclasts, so as to decrease the bone resorption and prevent the osteoporosis.

The present invention provides a salicylanilide-derived small molecule, which structure is selected from formula I or formula II:

The pharmaceutical composition of the present invention comprises, but not limited to, (a) a compound, which structure is selected from formula I or formula II:

I

II (b) a pharmaceutical acceptable salt and carrier of the compounds.

In the best embodiment, the R of the formula I or formula II is selected from the group of H and OCxHy, wherein the x and y of the OCxHy is any positive integer; the R' of the formula I or formula II is selected from the group consisting of Halogen, wherein the Halogen is F, Cl, Br, I or At; the R" of the formula I is selected from the group consisting of H, OCxHy and 2,4-difluorobenzyl, wherein the x and y of the OCxHy is any positive integer.

In the best embodiment, the pharmaceutical acceptable carrier is excipient, diluents, thickeners, filler, binder, disintegrants, lubricant, oil or non-oil base, surfactant, suspending agent, gelling agent, adjuvant, anti-corrosive agent, anti-oxidant, stabilizer, coloring agent or flavor. Wherein the excipient can be, but not limited to, microcrystalline cellulose, polyvinylpyrrolidone (PVP), modified starches, sodium starch glycolate, gelatinized starches, polyethylene glycol (PEG), polyvinyl alcohol, hydroxypropyl cellulose, methylcellulose, hydroxymethyl cellulose, hydroxypropyl methylcellulose.

In the best embodiment, the salt can be physiological acceptable salt of inorganic acid, inorganic base, organic acid or organic base.

In the best embodiment, the composition can be powder, granule, liquid, gel or cream.

In the best embodiment, the composition is administrated through oral, transdermal, injection, or inhalational manner.

The present invention provides a synthesis method of pharmaceutical composition of salicylanilide-derived small molecule, wherein a compound of formula I is synthesized by a compound of formula III:

III

I

In the best embodiment, the R of the formula I or formula III is selected from the group consisting of H and OCxHy, wherein the x and y of the OCxHy is any positive integer; the R' of the formula I is selected from the group consisting of Halogen, wherein the Halogen is F, Cl, Br, I or At; and the R" of the formula I is selected from the group consisting of H, OCxHy and 2,4-difluorobenzyl, wherein the x and y of the OCxHy is any positive integer.

In the best embodiment, the compound of formula III is salicylic acid, and compound of formula III, tetrahydrofuran and thionyl chloride can synthesize a intermediate, the intermediate, amine and tetrahydrofuran can synthesize a compound of formula I. Wherein the amine is 4-chloro-2-fluorobenzenamine or 2,4-difluoroaniline.

The present invention also provides a synthesis method of pharmaceutical composition of salicylanilide-derived small molecule, wherein a compound of formula II is synthesized by a compound of formula I:

I

II

In the best embodiment, the compound of formula II is synthesized by the compound of formula I, anhydrous pyridine and methyl chloroformate.

In the best embodiment, the pharmaceutical composition can be used as an osteoporosis therapeutic agent, an osteoarthritis therapeutics agent or an anti-inflammatory agent.

As mentioned above, all the substitutes of the salicylanilide-derived derivatives small molecules in the present invention are listing as follows

TABLE 1

The R, R', R" of the compounds of the present invention

| series | compounds | R | R' | R" |
|---|---|---|---|---|
| I | compound 1a | H | Cl | H |
| I | compound 1b | H | Cl | OCH$_3$ |

TABLE 1-continued

The R, R', R'' of the compounds of the present invention

| series | compounds | R | R' | R'' |
|---|---|---|---|---|
| I | compound 1c | H | Cl | 2,4-difluorobenzyl |
| II | compound 1d | H | Cl | |
| I | compound 2a | OCH$_3$ | Cl | H |
| I | compound 2b | OCH$_3$ | Cl | OCH$_3$ |
| I | compound 2c | OCH$_3$ | Cl | 2,4-difluorobenzyl |
| II | compound 2d | OCH$_3$ | Cl | |
| I | compound 3a | H | F | H |
| I | compound 3b | H | F | OCH$_3$ |
| I | compound 3c | H | F | 2,4-difluorobenzyl |
| II | compound 3d | H | F | |
| I | compound 4a | OCH$_3$ | F | H |
| I | compound 4b | OCH$_3$ | F | OCH$_3$ |
| I | compound 4c | OCH$_3$ | F | 2,4-difluorobenzyl |
| II | compound 4d | OCH$_3$ | F | |

The recent studies showed that salicylanilide and aspirin have the inhibitory activity of NF-κB. The mechanism can affect the inhibition of osteoclastogenesis. Natural compounds, such as Paeonol of *Paeonia lactiflora Pallas*, Ikarisoside A of *Epimedium koreanum*, Bavachalcone of *Psoralea corylifolia*, etc., also can inhibit osteoclastogenesis. Besides, Indeno[1,2-c]quinoline derivatives, Benzopyranyl Tetracycles derivatives and 3-Amino-2-hydroxypropoxyisoflavone derivatives are also found have the inhibition ability. However, the mechanism and effects are still unclear. Therefore, synthesizing more compounds, which could apply to inhibit osteoclastogenesis and have the great help to inhibit the development of osteoporosis drugs.

Recently, we had selected a compound NDMC101 which could inhibit osteoclastogenesis, and it was proved to inhibit the expression of NFAT-c1 and the RANKL-induced phosphorylation of ERK, JNK and P38, so as to decrease the RANKL-induced phosphorylation of IκB and inhibit the NF-κB, p65. It could decrease the amount of RANKL-induced osteoclasts and decrease the resorption of osteoclasts. The modified structure of NDMC101 was tested for better effects. For example, the hydroxyl group was replaced by methoxy group or connected to 2,4-difluorobenzyl, which were hydrophobic group and identified the effects of hydroxyl group on osteoclastogenesis (b and c series). The N-(4-chloro-2-fluorophenyl)benzamide was cyclized to identify the difference of pharmacological activity of bicyclic main structure (d series). Besides, we used another starting material (2-hydroxy-4-methoxybenzoic acid) to synthesize b, c, d series which was added the methoxy group on C4. This structure was modified from natural product Paeonol (both C4 had methoxy group). Moreover, the 4-chloro-2-fluoroaniline on compound 1a was replaced by 2,4-difluoroaniline, and synthesize the b, c, d series, and investigated the difference between chloride group and fluoride group.

The following examples 1~16 are the specific synthesis methods of the compounds of the present invention:

Example 1

N-(4-chloro-2-fluorophenyl)-2-hydroxybenzamide (compound 1a, NDMC101)

To a solution of salicylic acid (1.38 g, 10 mmole) in tetrahydrofuran (40 mL) was added thionyl chloride (2.5 mL, 35 mmole) and refluxed 3 hr. The mixture was steamed (110° C.) by Dean-Stark. The residue was directly reacted with 4-chloro-2-fluorobenzenamine (1.1 mL, 10 mmole) in THF (40 mL) for 14 hr. The reaction mixture was concentrated and extracted with ethyl acetate, dried over anhydrous magnesium sulfate. Recrystallization of desired products from hot dichloromethane afforded the compound.

The pure compound was obtained as white powder (yield 46%). Mp 184-185° C. $^1$H NMR (300 MHz, CDCl$_3$): ppm 6.92-6.98 (m, 1H), 7.05 (dd, J=8.4, 1.2 Hz, 1H), 7.18-7.23 (m, 2H), 7.45-7.50 (m, 1H), 7.52 (dd, J=8.1, 1.5 Hz, 1H), 8.27-8.33 (m, 1H), 8.13 (br, 1H), 11.66 (s, 1H). HRMS (EI) m/z calcd for C$_{13}$H$_9$ClFNO$_2$$^+$ [M]$^+$: 265.0306. Found: 265.0305.

Example 2

N-(4-chloro-2-fluorophenyl)-2-methoxybenzamide (compound 1b)

To a solution of compound 1a (0.53 g, 2 mmole) in anhydrous acetone (10 mL) were added potassium carbonate (0.69 g, 5 mmole) and iodomethane (0.28 mL, 4.4 mmole) and refluxed 8 hr. After cooled to room temperature, the reaction mixture was filtered through Celite and concentrated. The residue was extracted with ethyl acetate and dried over anhydrous magnesium sulfate, then concentrated and recrystallized with hot methanol.

The pure compound was obtained as white powder (yield 81%). Mp 111-112° C. $^1$H NMR (300 MHz, CDCl$_3$): ppm 4.07 (s, 3H), 7.05 (d, J=8.4 Hz, 1H), 7.02-7.18 (m, 3H), 7.49-7.55 (m, 1H), 8.29 (dd, J=7.8, 1.8 Hz, 1H), 8.55-8.61 (m, 1H), 10.35 (br, 1H). HRMS (EI) m/z calcd for C$_{14}$H$_{11}$ClFNO$_2$$^+$ [M]$^+$: 279.0462. Found: 279.0458

Example 3

N-(4-chloro-2-fluorophenyl)-2-((2,4-difluorobenzyl)oxy)benzamide (compound 1c)

To a solution of compound 1a (0.53 g, 2 mmole) in anhydrous acetone (10 mL) were added potassium carbonate (0.69 g, 5 mmole) and 2,4-difluorobenzyl bromide (0.56 mL, 4.4 mmole) and refluxed 8 hr. After cooled to room temperature, the reaction mixture was filtered through Celite and concentrated. The residue was extracted with ethyl acetate and dried over anhydrous magnesium sulfate, then concentrated and recrystallized with hot methanol.

The pure compound was obtained as white powder (yield 75%). Mp 121-122° C. $^1$H NMR (300 MHz, CDCl$_3$): ppm 5.29 (s, 2H), 6.87-6.96 (m, 2H), 7.03 (dd, J=7.8, 2.4 Hz, 1H), 7.10-7.20 (m, 3H), 7.42-7.56 (m, 2H), 8.30 (dd, J=7.8, 1.8 Hz, 1H), 8.53 (t, J=8.7 Hz, 1H), 10.04 (br, 1H). HRMS (ESI) m/z calcd for C$_{20}$H$_{14}$ClF$_3$NO$_2$$^+$ [M+H]$^+$: 392.0655. Found: 392.0673.

Example 4

3-(4-chloro-2-fluorophenyl)-2H-benzo[e][1,3]oxazine-2,4(3H)-dione (compound 1d)

Methyl chloroformate (0.1 mL, 1.2 mmole) was added dropwise to a stirred solution of compound 1a (0.266 g, 1 mmole) in dry pyridine (8 mL) at 0° C. The mixture was refluxed for 2 hr. After 16 hr stirring at room temperature, the pH of the reaction mixture was adjusted to pH=6 from 1 M HCl$_{(aq)}$. The resulting white mixture was cooled to obtain solid compound. The product was filtered off and recrystallized from hot ethanol.

The pure compound was obtained as white powder (yield 52%). Mp 178-179° C. $^1$H NMR (300 MHz, CDCl$_3$): ppm 7.30-7.34 (m, 3H), 7.36-7.39 (m, 1H), 7.40-7.46 (m, 1H), 7.75-7.81 (m, 1H), 8.13 (dd, J=7.8, 1.5 Hz, 1H). HRMS (ESI) m/z calcd for $C_{14}H_8ClFNO_3^+$ [M+H]$^+$: 292.0177. Found: 292.0181.

Example 5

N-(4-chloro-2-fluorophenyl)-2-hydroxy-4-methoxybenzamide (compound 2a)

To a solution of 2-hydroxy-4-methoxybenzoic acid (1.68 g, 10 mmole) in tetrahydrofuran (40 mL) was added thionyl chloride (2.5 mL, 35 mmole) and refluxed 3 hr. The mixture was steamed (110° C.) by Dean-Stark. The residue was directly reacted with 4-chloro-2-fluorobenzenamine (1.1 mL, 10 mmole) in THF (40 mL) for 14 hr. The reaction mixture was concentrated and extracted with ethyl acetate, dried over anhydrous magnesium sulfate. Recrystallization of desired products from hot dichloromethane afforded the compound.

The pure compound was obtained as white powder (yield 41%). Mp 186-187° C. $^1$H NMR (300 MHz, CDCl$_3$): ppm 3.85 (s, 3H), 6.48-6.52 (m, 2H), 7.16-7.21 (m, 2H), 7.41 (dd, J=7.2, 2.1 Hz, 1H), 7.93 (br, 1H), 8.25-8.31 (m, 1H), 12.07 (s, 1H). HRMS (ESI) m/z calcd for $C_{14}H_{12}ClFNO_3^+$ [M+H]$^+$: 296.0490. Found: 296.0491.

Example 6

N-(4-chloro-2-fluorophenyl)-2,4-dimethoxybenzamide (compound 2b)

To a solution of compound 2a (0.59 g, 2 mmole) in anhydrous acetone (10 mL) were added potassium carbonate (0.69 g, 5 mmole) and iodomethane (0.28 mL, 4.4 mmole) and refluxed 8 hr. After cooled to room temperature, the reaction mixture was filtered through Celite and concentrated. The residue was extracted with ethyl acetate and dried over anhydrous magnesium sulfate, then concentrated and recrystallized with hot methanol.

The pure compound was obtained as white powder (yield 83%). Mp 155-156° C. $^1$H NMR (300 MHz, CDCl$_3$): ppm 3.87 (s, 3H), 4.03 (s, 3H), 6.52 (d, J=2.4 Hz, 1H), 6.64 (dd, J=8.7, 2.4 Hz, 1H), 7.10-7.15 (m, 2H), 8.23 (d, J=8.7 Hz, 1H), 8.54-8.60 (m, 1H), 10.18 (br, 1H). HRMS (ESI) m/z calcd for $C_{15}H_{14}ClFNO_3^+$ [M+H]$^+$: 310.0646. Found: 310.0655.

Example 7

N-(4-chloro-2-fluorophenyl)-2-((2,4-difluorobenzyl)oxy)-4-methoxybenzamide (compound 2c)

To a solution of compound 2a (0.59 g, 2 mmole) in anhydrous acetone (10 mL) were added potassium carbonate (0.69 g, 5 mmole) and 2,4-difluorobenzyl bromide (0.56 mL, 4.4 mmol) and refluxed 8 hr. After cooled to room temperature, the reaction mixture was filtered through Celite and concentrated. The residue was extracted with ethyl acetate and dried over anhydrous magnesium sulfate, then concentrated and recrystallized with hot methanol.

The pure compound was obtained as white powder (yield 66%). Mp 134-135° C. $^1$H NMR (300 MHz, CDCl$_3$): ppm 3.87 (s, 3H), 5.25 (s, 2H), 6.64 (d, J=2.1, 1H), 6.68 (dd, J=8.7, 2.1, 1H), 6.86-6.97 (m, 2H), 7.01 (dd, J=10.8, 2.4 Hz, 1H), 7.10 (dd, J=9.0, 2.1 Hz, 1H), 7.42-7.49 (m, 1H), 8.25 (d, J=8.7 Hz, 1H), 8.53 (t, J=8.7 Hz, 1H), 9.91 (br, 1H). HRMS (ESI) m/z calcd for $C_{21}H_{16}ClF_3NO_3^+$ [M+H]$^+$: 422.0771. Found: 422.0778.

Example 8

3-(4-chloro-2-fluorophenyl)-7-methoxy-2H-benzo[e][1,3]oxazine-2,4(3H)-dione (compound 2d)

Methyl chloroformate (0.1 mL, 1.2 mmole) was added dropwise to a stirred solution of compound 2a (0.295 g, 1 mmole) in dry pyridine (8 mL) at 0° C. The mixture was refluxed for 2 hr. After 16 hr stirring at room temperature, the pH of the reaction mixture was adjusted to pH=6 from 1 M HCl$_{(aq)}$. The resulting white mixture was cooled to obtain solid compound. The product was filtered off and recrystallized from hot ethanol. The residue was extracted with ethyl acetate and dried over anhydrous magnesium sulfate, then concentrated and recrystallized with hot methanol.

The pure compound was obtained as white powder (yield 41%). Mp 203-204° C. $^1$H NMR (300 MHz, CDCl$_3$): ppm 3.94 (s, 3H), 6.97 (d, J=2.1 Hz, 1H), 6.95 (dd, J=9.0, 2.1 Hz, 1H), 7.29-7.32 (m, 3H), 8.02 (d, J=9.0 Hz, 1H). HRMS (ESI) m/z calcd for $C_{15}H_{10}ClFNO_4^+$ [M+H]$^+$: 322.0282. Found: 322.0295.

Example 9

N-(2,4-difluorophenyl)-2-hydroxybenzamide (compound 3a)

To a solution of salicylic acid (1.38 g, 10 mmole) in tetrahydrofuran (40 mL) was added thionyl chloride (2.5 mL, 35 mmole) and refluxed 3 hr. The mixture was steamed (110° C.) by Dean-Stark. The residue was directly reacted with 2,4-difluorobenzenamine (1 mL, 10 mmole) in THF (40 mL) for 3 hr. The reaction mixture was concentrated and extracted with ethyl acetate, dried over anhydrous magnesium sulfate. Recrystallization of desired products from hot dichloromethane afforded the compound.

The pure compound was obtained as white powder (yield: 40%). Mp 186-187° C. $^1$H NMR (300 MHz, CDCl$_3$): ppm 6.91-6.99 (m, 3H), 7.05 (dd, J=8.4, 0.9 Hz, 1H), 7.45-7.51 (m, 1H), 7.53 (dd, J=8.1, 1.5 Hz, 1H), 8.05 (br, 1H), 8.21-8.29 (m, 1H), 11.72 (s, 1H). HRMS (ESI) m/z calcd for $C_{13}H_{13}F_2NO_2^+$ [M+H]$^+$: 250.0680. Found: 250.0666.

Example 10

N-(2,4-difluorophenyl)-2-methoxybenzamide (compound 3b)

To a solution of compound 3a (0.50 g, 2 mmole) in anhydrous acetone (10 mL) were added potassium carbonate (0.69 g, 5 mmole) and iodomethane (0.28 mL, 4.4 mmol) and refluxed 8 hr. After cooled to room temperature, the reaction mixture was filtered through Celite and concentrated. The residue was extracted with ethyl acetate and dried over anhydrous magnesium sulfate, then concentrated and recrystallized with hot methanol.

The pure compound was obtained as yellow powder (yield 48%). Mp 86-87° C. $^1$H NMR (300 MHz, CDCl$_3$): ppm 4.07 (s, 3H), 6.85-6.94 (m, 2H), 7.04 (d, J=1.8 Hz, 1H), 7.12-7.17 (m, 1H), 7.49-7.54 (m, 1H), 8.29 (dd, J=7.8, 1.8 Hz, 1H), 8.52-8.60 (m, 1H), 10.24 (br, 1H). HRMS (ESI) m/z calcd for $C_{14}H_{12}F_2NO_2^+$ [M+H]$^+$: 264.0836. Found: 264.0827

Example 11

2-((2,4-difluorobenzyl)oxy)-N-(2,4-difluorophenyl)benzamide (compound 3c)

To a solution of compound 3a (0.50 g, 2 mmole) in anhydrous acetone (10 mL) were added potassium carbonate (0.69 g, 5 mmole) and 2,4-difluorobenzyl bromide (0.56 mL, 4.4 mmole) and refluxed 8 hr. After cooled to room temperature, the reaction mixture was filtered through Celite and concentrated. The residue was extracted with ethyl acetate and dried over anhydrous magnesium sulfate, then concentrated and recrystallized with hot methanol.

The pure compound was obtained as white powder (yield 34%). Mp 135-136° C. $^1$H NMR (300 MHz, CDCl$_3$): ppm 5.28 (s, 2H), 6.74-6.83 (m, 1H), 6.84-6.96 (m, 3H), 7.12-7.20 (m, 2H), 7.42-7.54 (m, 2H), 8.30 (dd, J=7.8, 1.8 Hz, 1H), 8.47-8.55 (m, 1H), 9.95 (br, 1H). HRMS (ESI) m/z calcd for C$_{20}$H$_{14}$F$_4$NO$_3^+$ [M+H]$^+$: 376.0961. Found: 376.0955.

Example 12

3-(2,4-difluorophenyl)-2H-benzo[e][1,3]oxazine-2,4(3H)-dione (compound 3d)

Methyl chloroformate (0.1 mL, 1.2 mmole) was added dropwise to a stirred solution of compound 3a (0.50 g, 2 mmole) in dry pyridine (8 mL) at 0° C. The mixture was refluxed for 2 hr. After 16 hr stirring at room temperature, the pH of the reaction mixture was adjusted to pH=6 from 1 M HCl$_{(aq)}$. The resulting white mixture was cooled to obtain solid compound. The product was filtered off and recrystallized from hot ethanol.

The pure compound was obtained as white powder (yield 38%). Mp 182-183° C. $^1$H NMR (300 MHz, CDCl$_3$): ppm 7.00-7.06 (m, 2H), 7.31-7.39 (m, 2H), 7.40-7.45 (m, 1H), 7.75-7.81 (m, 1H), 8.13 (dd, J=7.8, 1.8 Hz, 1H). HRMS (ESI) m/z calcd for C$_{14}$H$_8$F$_2$NO$_3^+$ [M+H]$^+$: 276.0472. Found: 276.0454.

Example 13

N-(2,4-difluorophenyl)-2-hydroxy-4-methoxybenzamide (compound 4a)

To a solution of 2-hydroxy-4-methoxybenzoic acid (1.68 g, 10 mmole) in tetrahydrofuran (40 mL) was added thionyl chloride (2.5 mL, 35 mmole) and refluxed 3 hr. The mixture was steamed (110° C.) by Dean-Stark. The residue was directly reacted with 2,4-difluorobenzenamine (1 mL, 10 mmole) in THF (40 mL) for 14 hr. The reaction mixture was concentrated and extracted with ethyl acetate, dried over anhydrous magnesium sulfate. Recrystallization of desired products from hot dichloromethane afforded the compound.

The pure compound was obtained as white powder (yield 45%). Mp 180-181° C. $^1$H NMR (300 MHz, CDCl$_3$): ppm 3.85 (s, 3H), 6.48-6.51 (m, 2H), 6.91-6.97 (m, 2H), 7.41-7.44 (m, 2H), 7.85 (br, 1H), 8.18-8.26 (m, 1H), 12.14 (s, 1H). HRMS (ESI) m/z calcd for C$_{14}$H$_{12}$F$_2$NO$_3^+$ [M+H]$^+$: 280.0785. Found: 280.0773.

Example 14

N-(2,4-difluorophenyl)-2,4-dimethoxybenzamide (compound 4b)

To a solution of compound 4a (0.56 g, 2 mmole) in anhydrous acetone (10 mL) were added potassium carbonate (0.69 g, 5 mmole) and iodomethane (0.28 mL, 4.4 mmole) and refluxed 8 hr. After cooled to room temperature, the reaction mixture was filtered through Celite and concentrated. The residue was extracted with ethyl acetate and dried over anhydrous magnesium sulfate, then concentrated and recrystallized with hot methanol.

The pure compound was obtained as white powder (yield 41%). Mp 138-139° C. $^1$H NMR (300 MHz, CDCl$_3$): ppm 3.88 (s, 3H), 4.03 (s, 3H), 6.54 (d, J=2.1 Hz, 1H), 6.65 (dd, J=9, 2.1 Hz, 1H), 6.84-6.91 (m, 2H), 8.24 (d, J=8.7 Hz, 1H), 8.46-8.58 (m, 1H), 10.09 (br, 1H). HRMS (ESI) m/z calcd for C$_{15}$H$_{14}$F$_2$NO$_3^+$ [M+H]$^+$: 294.0942. Found: 294.0938.

Example 15

2-((2,4-difluorobenzyl)oxy)-N-(2,4-difluorophenyl)-4-methoxybenzamide (compound 4c)

To a solution of compound 4a (0.56 g, 2 mmole) in anhydrous acetone (10 mL) were added potassium carbonate (0.69 g, 5 mmole) and 2,4-difluorobenzyl bromide (0.56 mL, 4.4 mmol) and refluxed 8 hr. After cooled to room temperature, the reaction mixture was filtered through Celite and concentrated. The residue was extracted with ethyl acetate and dried over anhydrous magnesium sulfate, then concentrated and recrystallized with hot methanol.

The pure compound was obtained as white powder (yield 36%). Mp 131-132° C. $^1$H NMR (300 MHz, CDCl$_3$): ppm 3.88 (s, 3H), 5.26 (s, 2H), 6.64-6.96 (m, 6H), 7.42-7.50 (m, 1H), 8.26 (d, J=8.7 Hz, 1H), 8.46-8.54 (m, 1H), 9.84 (br, 1H). HRMS (ESI) m/z calcd for C$_{21}$H$_{16}$F$_4$NO$_3^+$ [M+H]$^+$: 406.1066. Found: 406.1067.

Example 16

3-(2,4-difluorophenyl)-7-methoxy-2H-benzo[e][1,3]oxazine-2,4(3H)-dione (compound 4d)

Methyl chloroformate (0.1 mL, 1.2 mmole) was added dropwise to a stirred solution of compound 4a (0.28 g, 1 mmole) in dry pyridine (8 mL) at 0° C. The mixture was refluxed for 2 hr. After 16 hr stirring at room temperature, the pH of the reaction mixture was adjusted to pH=6 from 1 M HCl$_{(aq)}$. The resulting white mixture was cooled to obtain solid compound. The product was filtered off and recrystallized from hot ethanol. The residue was extracted with ethyl acetate and dried over anhydrous magnesium sulfate, then concentrated and recrystallized with hot methanol.

The pure compound was obtained as white powder (yield 34%). Mp 138-139° C. $^1$H NMR (300 MHz, CDCl$_3$): ppm 3.93 (s, 3H), 6.79 (d, J=2.4 Hz, 1H), 6.94 (dd, J=8.7, 2.4 Hz, 1H), 6.99-7.05 (m, 2H), 7.30-7.36 (m, 1H), 8.02 (d, J=8.7 Hz, 1H). HRMS (ESI) m/z calcd for C$_{15}$H$_{10}$F$_2$NO$_4^+$ [M+H]$^+$: 306.0578. Found: 306.0560.

The following examples is the pharmacological activity of compounds 1-16:

Example 17

The Pharmacological Activity Test and Result

Cell viability was measured by MTT assay in RAW 264.7 cells upon treatment with 10 μM compounds for 24 hr. CC$_{50}$ (the cytotoxic concentration that produces 50% cell survival) were identified in this example. The result was showed in Table 1. The cell viability was 93.0±3.1% upon treatment with compound 1a at 10 μM, which proved that the inhibition of differentiation effect is not caused by cytotoxic reaction. However, CC$_{50}$ is 21.3±3.4 μM, it represented that the cell viability was 50% at 21.3 μM and the result was still revealed cytotoxicity for RAW 264.7. The newly synthesized compounds, which was chemically modified to decreased the cytotoxicity, wherein the most effective compound 1d ($CC_{50}$>40 04), compound 2a ($CC_{50}$=32.3±4.9 μM), compound 2d ($CC_{50}$>40 μM), compound 4a ($CC_{50}$>40 μM) would evaluate the cell viability obviously, which proved that the inhibition of differentiation effect is not caused by cytotoxic reaction.

TABLE 1

The amounts of cell viability and Osteoclastogenesis of RAW 264.7 affected by compounds

| compounds | Cell viability | | Osteoclastogenesis |
|---|---|---|---|
| | Survival rate at 10 μM (%) | $CC_{50}$ (μM) | TRAP$^+$ MNC$_S$ at 10 μM (%) |
| 1a | 93.0 ± 3.1 | 21.3 ± 3.4 | 49.4 ± 5.4 |
| 1b | 101.8 ± 4.5 | >40 | 86.0 ± 9.9 |
| 1c | 107.2 ± 4.5 | >40 | 74.6 ± 6.2 |
| 1d | 97.9 ± 2.0 | >40 | 3.4 ± 2.1 |
| 2a | 103.0 ± 2.8 | 32.3 ± 4.9 | 23.8 ± 3.4 |
| 2b | 52.9 ± 2.8 | 13.6 ± 1.2 | 60.2 ± 3.6 |
| 2c | 107.3 ± 4.4 | >40 | 68.7 ± 4.6 |
| 2d | 100.5 ± 2.4 | >40 | 36.0 ± 1.8 |
| 3a | 104.0 ± 3.6 | >40 | 85.9 ± 6.2 |
| 3b | 108.5 ± 4.0 | >40 | 89.1 ± 5.1 |
| 3c | 101.1 ± 3.2 | >40 | 97.6 ± 6.0 |
| 3d | 105.0 ± 6.3 | >40 | 69.8 ± 7.7 |
| 4a | 105.2 ± 4.7 | >40 | 41.3 ± 8.6 |
| 4b | 102.5 ± 9.3 | >40 | 93.0 ± 7.7 |
| 4c | 106.0 ± 8.8 | >40 | 66.2 ± 8.1 |
| 4d | 102.3 ± 9.1 | >40 | 87.9 ± 9.1 |
| Salicylic acid | 99.8 ± 12.2 | >40 | 99.8 ± 7.5 |
| 2-hydroxy-4-methoxy-benzoic acid | 99.4 ± 7.6 | >40 | 79.6 ± 8.3 |

The Osteoclastogenesis amounts were also showed in Table 1. Tartrate-resistant acid phosphatase (TRAP) staining and activity assay was used to confirm the inhibitory activity of synthesized compounds. The murine RAW 264.7 cell was an osteoclast precursor cell. RAW 264.7 cells were cultured in DMEM (Gibco BRL), 10% FBS, Penicillin (100 U/L), Streptomycin (100 U/L), 5% $CO_2$, 37° C. To induce the murine RAW 264.7 cells differentiation, the cells were cultured in 96-well culture dish $10^4$ cell per dish with α-MEM, 10% FBS, 2 mM L-glutamate, Penicillin (100 U/L), Streptomycin (100 U/L), with or without 100 ng/mL RANKL for 5 days, and added or not added tested drug, replaced the fresh medium at 3 day. The cells were TRAP$^+$ stained and analyzed the activity, then washed the cells by PBS and fixed by 3.7% formaldehyde for 30 minutes, then washed by PBS. The cells were reacted in Leukocyte Acid Phosphatase Assay kit (Sigma) at 37° C. for 1 hr, and washed by distilled water for three times and counted the multinucleated cells numbers by microscopy.

After treatment with RANKL and 10 μM compounds in RAW 264.7, the osteoclasts were counted percentage of the TRAP$^+$ cells (TRAP$^+$ MNCS %, the denominator was the number of cells which was treated with RANKL but without drug, and the numerator was the number of cells which was treated with RANKL and drug). The starting material, salicylic acid and 2-hydroxy-4-methoxy-benzoic acid did not perform significant inhibitory activity. However, after treated with 10 μM modified compound 1a, the osteoclasts percentage was 49.4±5.4%. Moreover, after further modified, the 10 μM compounds 1d (3.4±2.1%), 2a (23.8±3.4%), 2d (36.0±1.8%), 4a (41.3±8.6%) performed better inhibitory activity.

Figure 1:
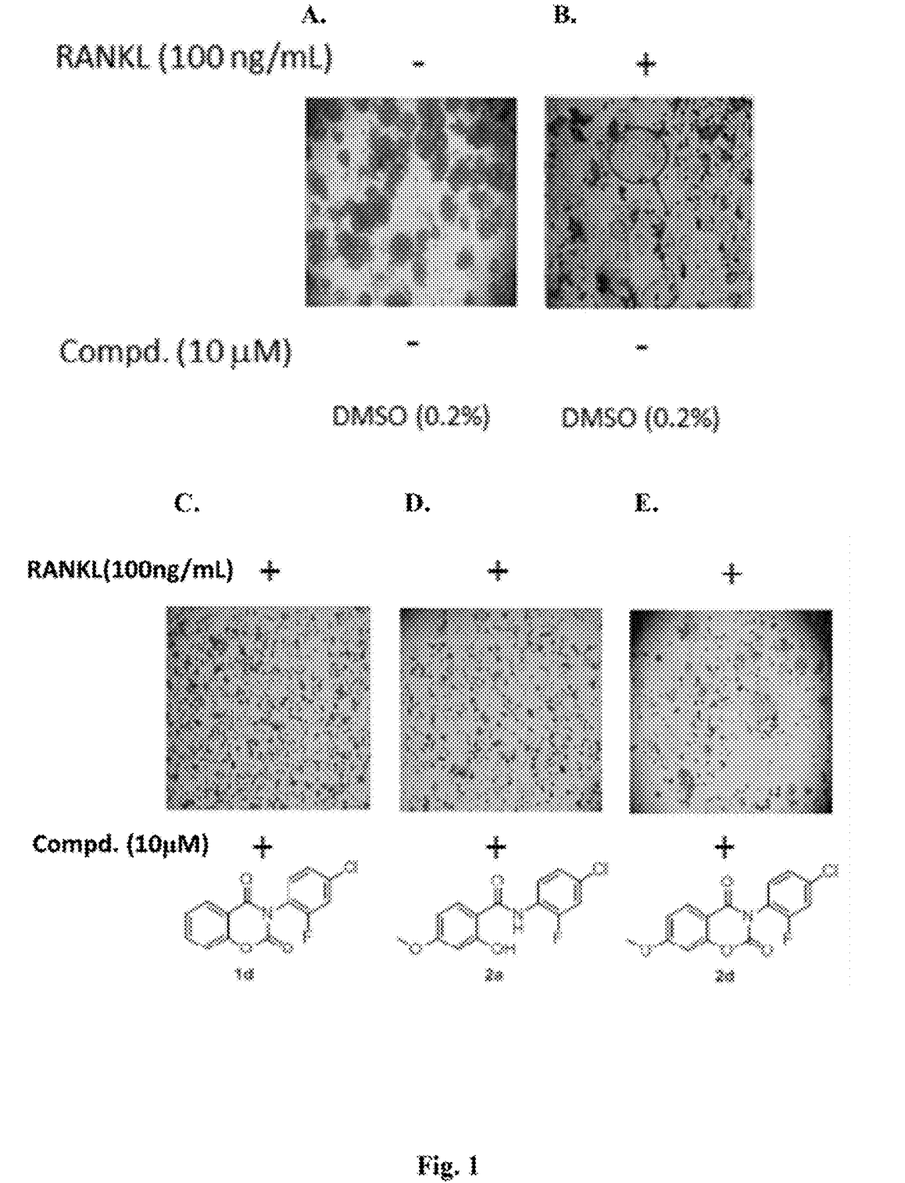

The result of mentioned TRAP staining and activity analysis was shown in FIG. 1, wherein FIG. 1A showed the cells treated without RANKL and no differentiation; FIG. 1B showed the cells treated with RANKL and triggered the differentiated osteoclasts to fusion as multinucleated state; C, D and E showed the cells treated with RANKL and added in 10 μM compound 1d, 2a and 2d, which showed the significant inhibition of differentiation.

In pit formation assay, RAW 264.7 cells were cultured in DMEM (Gibco BRL) 10% FBS, Penicillin (100 U/L), streptomycin (100 U/L), 5% CO2 at 37° C. To induce the murine RAW 264.7 cell differentiation, the cells were cultured in 96-well culture dish $10^4$ cell per dish with α-MEM, 10% FBS, 2 mM L-glutamate, Penicillin (100 U/L), Streptomycin (100 U/L), with or without 100 ng/mL RANKL for 5 days in the present or absent tested drug, replaced the fresh medium at 3 day. The 24-well plate were washed by PBS and added in 0.5 mL/well chloride solution, stood at room-temperature for 10 minutes for destroying the cell, then stained with 0.1% Toluidine Blue 0.5 mL/well, and washed by distilled water for three times and photographed under microscopy.

Figure 2:
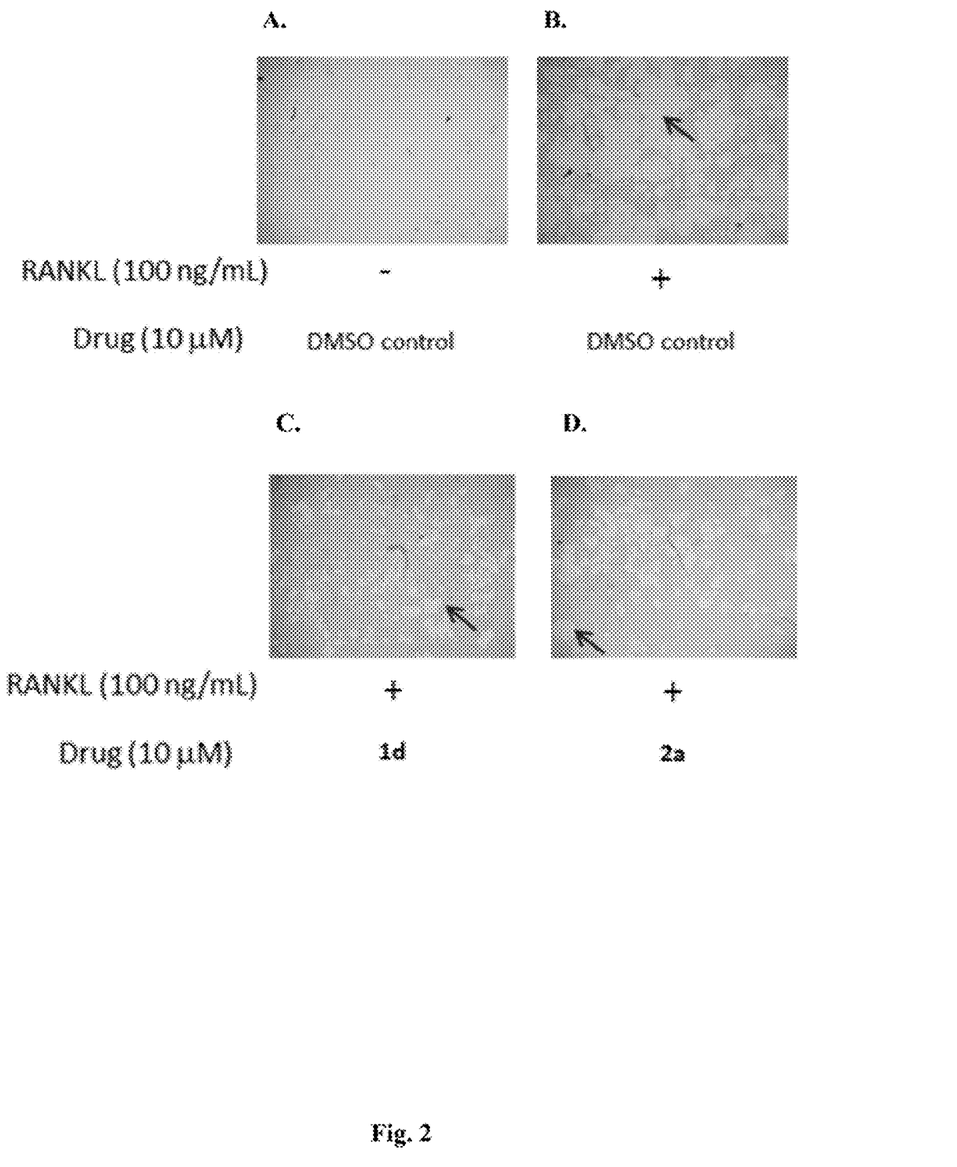

As shown in FIG. 2, wherein A showed the cells treated without RANKL and no differentiation; B showed the cells treated with RANKL and triggered the differentiated osteoclasts, the mark of osteoclasts as arrows; C and D showed the cells treated with RANKL and 10 μM tested compounds 1d and 2a, the mark was narrow and the resorption hole was reduced as arrows. The result proved that the compounds would not only inhibit the osteoclasts activity, but also reduce the bone resorption activity significantly.

What is claimed is:

1. A salicylanilide-derived small molecule, as shown in formula II:

wherein R of formula II is selected from the group consisting of H and $OCH_3$; R' of formula II is a Halogen, wherein the Halogen is F, Cl, Br, I or At.

2. A pharmaceutical composition of salicylanilide-derived small molecule, which comprises:

(a) a compound as shown in formula II:

(b) a pharmaceutical acceptable salt and carrier of the said compounds, wherein R of formula II is selected from the group consisting of H and $OCH_3$; R' of the formula II is a Halogen, wherein the Halogen is F, Cl, Br, I or At.

3. The pharmaceutical composition of claim 2, wherein the pharmaceutical acceptable carrier is an excipient, diluent, thickener, filler, binder, disintegrant, lubricant, oil or non-oil base, surfactant, suspending agent, gelling agent, adjuvant, anti-corrosive agent, anti-oxidant, stabilizer, coloring agent or flavoring agent.

4. The pharmaceutical composition of claim 2, wherein the salt is physiological acceptable salt of inorganic acid, inorganic base, organic acid or organic base.

5. The pharmaceutical composition of claim 2, wherein said composition is a powder, granule, liquid, gel or cream.

6. The pharmaceutical composition of claim 2, wherein said composition is administrated through oral, transdermal, injection, or inhalational manner.

7. A synthesis method of salicylanilide-derived small molecule, wherein a compound of formula II is synthesized by a compound of formula I:

wherein R of the formula I or formula II is selected from the group consisting of H and $OCH_3$; R' of the formula I or formula II is a Halogen, wherein the Halogen is F, Cl, Br, I or At; and R" of the formula I is H, the method comprising:
adding methyl chloroformate to a solution of a compound of formula I and anhydrous pyridine and refluxing the mixture to obtain a compound of formula II.

* * * * *